(12) United States Patent
Konosonoks et al.

(10) Patent No.: US 10,987,344 B2
(45) Date of Patent: Apr. 27, 2021

(54) PHARMACEUTICAL COMPOSITION CAPABLE OF THE INCORPORATION OF LENALIDOMIDE IN VARIOUS CRYSTALLINE MODIFICATIONS

(71) Applicant: GRINDEKS, A JOINT STOCK COMPANY, Riga (LV)

(72) Inventors: Armands Konosonoks, Riga (LV); Kestutis Merkys, Riga (LV)

(73) Assignee: GRINDEKS, A JOINT STOCK COMPANY, Riga (LV)

( * ) Notice: Subject to any disclaimer, the term of this patent is extended or adjusted under 35 U.S.C. 154(b) by 0 days.

(21) Appl. No.: 15/754,414

(22) PCT Filed: Aug. 26, 2016

(86) PCT No.: PCT/EP2016/070165
§ 371 (c)(1),
(2) Date: Feb. 22, 2018

(87) PCT Pub. No.: WO2017/032870
PCT Pub. Date: Mar. 2, 2017

(65) Prior Publication Data
US 2018/0243283 A1  Aug. 30, 2018

(30) Foreign Application Priority Data

Aug. 27, 2015 (EP) .................... 15182621

(51) Int. Cl.
*C07D 401/14* (2006.01)
*A61K 31/454* (2006.01)
*A61K 9/48* (2006.01)
*A61K 9/14* (2006.01)

(52) U.S. Cl.
CPC ............ *A61K 31/454* (2013.01); *A61K 9/141* (2013.01); *A61K 9/146* (2013.01); *A61K 9/48* (2013.01); *A61K 9/4858* (2013.01); *A61K 9/4866* (2013.01)

(58) Field of Classification Search
CPC .................................................. C07D 401/04
See application file for complete search history.

(56) References Cited

U.S. PATENT DOCUMENTS

| 9,119,786 B2 * | 9/2015 | Schwab ............... C07D 417/12 |
| 2011/0021567 A1 * | 1/2011 | Devarakonda ....... C07D 209/46 514/323 |
| 2012/0046315 A1 * | 2/2012 | Rimkus ................ A61K 9/1623 514/323 |
| 2016/0194301 A1 * | 7/2016 | Devarakonda ....... C07D 209/46 514/323 |

FOREIGN PATENT DOCUMENTS

| CN | 101537184 A * | 9/2009 | |
| DE | 102008057284 | 5/2010 | |
| WO | WO2014160686 | 5/2010 | |
| WO | WO-2010129636 A2 * | 11/2010 | ............. A61K 31/40 |
| WO | WO-2013012485 A2 * | 1/2013 | ......... A61K 31/4035 |

OTHER PUBLICATIONS

N. Rasenack et al., 9 Pharmaceutical Development and Technology, 1-13 (2004) (Year: 2004).*
P. Khadka et al., 9 Asian Journal of Pharmaceutical Sciences, 304-316 (2014) (Year: 2014).*
Bowen, P., "Particle size distribution measurement from millimeters to nanometers and from rods to platelets", Journal of Dispersion Science and Technology, vol. 23, No. 5, 2002, pp. 631-662.
International Search Report for PCT/EP2016/070165 dated Nov. 2, 2016.

* cited by examiner

*Primary Examiner* — John S Kenyon
(74) *Attorney, Agent, or Firm* — Hueschen and Sage

(57) ABSTRACT

The present invention relates to pharmaceutical compositions comprising the active substance Lenalidomide in one of the modifications selected from Lenalidomide base, a Lenalidomide salt, a Lenalidomide cocrystal or mixtures thereof, wherein the Lenalidomide particles have a particle size distribution ($d_{90}$) ranging from 1 μm to 100 μm.

18 Claims, 11 Drawing Sheets

PHARMACEUTICAL COMPOSITION CAPABLE OF THE INCORPORATION OF LENALIDOMIDE IN VARIOUS CRYSTALLINE MODIFICATIONS

FIELD OF THE INVENTION

The present invention relates to pharmaceutical compositions comprising the active substance Lenalidomide in one of the modifications selected from Lenalidomide base form A, Lenalidomide hydrochloride salt, Lenalidomide ammonium chloride cocrystal or mixtures thereof.

SUMMARY OF THE INVENTION

Lenalidomide is the International Non-proprietary Name (INN) of (RS)-3-(4-Amino-1-oxo 1,3-dihydro-2H-isoindol-2-yl)piperidine-2,6-dione which has the following chemical structure:

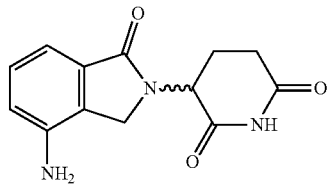 [SMILES: Nc1cccc2c1CN(C1CCC(=O)NC1=O)C2=O]

Lenalidomide is an anti-tumor agent registered and marketed under the trade names REVLIMID® and Ladevina® used for the treatment of multiple myeloma.

Several modifications of Lenalidomide have been described in the art.

For example, Lenalidomide base in the crystalline forms "A" and "B" (hereinafter also referred to as "Lenalidomide base form A" and "Lenalidomide base form B", respectively) are disclosed in WO 03/097040. However, this patent application does not disclose any specific pharmaceutical formulations comprising one of either form.

A Lenalidomide ammonium chloride cocrystal of Lenalidomide (hereinafter also referred to as Lenalidomide NH$_4$Cl cocrystal) has been disclosed in patent application WO 2013/012485 (Amplio Pharma). This patent application does not disclose any specific pharmaceutical formulations comprising an ammonium chloride cocrystal of Lenalidomide.

A Lenalidomide hydrochloride acid salt (hereinafter also referred to as Lenalidomide HCl salt) has been disclosed in US 2011/0060010 (Tianjin Hemay Bio-tech) and WO 2011/018101 (Synthon). Once more, no specific pharmaceutical formulations comprising a Lenalidomide hydrochloride acid salt are disclosed.

A DMSO-solvate of Lenalidomide is disclosed in WO 2010/056384. Also this application is silent regarding pharmaceutical formulations comprising the DMSO solvate of Lenalidomide.

For the development and registration of a generic version of any existing market product, certain regulatory requirements have to be met. Amongst them, the proof of bioequivalence is of major importance. In the case of Lenalidomide, the first step in aiming at bioequivalence of REVLIMID® is to approach its in-vitro dissolution profile. In order to do so, the knowledge of basic characteristic data such as the solubility of the Lenalidomide polymorphs and their dissolution characteristics is essential. For the development of any finished dosage form, it is generally favorable to establish methods and processes that allow the selection and use from a wide variety of the modifications of the active substances such as polymorphs, solvates, cocrystals and salts. Furthermore, it is favorable if relevant parameters can be adapted within broad ranges. Accordingly, the pharmaceutical formulation process shall be flexible not only as regards the choice of the modification of Lenalidomide and excipients as regards qualitative parameters, but shall also be flexible towards the ranges of active drug load, excipients etc. as regards quantitative parameters.

In the case of Lenalidomide, the prior art does remain silent about basic characteristic data of Lenalidomide polymorphs such as their solubility and dissolution characteristics, let alone their behavior when formulated with pharmaceutically acceptable excipients into finished dosage forms, leaving the skilled in the art in doubt about critical parameters of the manufacturing process of finished dosage forms of Lenalidomide.

Therefore, a first object of the present invention is the investigation of basic characteristics of different modifications of Lenalidomide and suitability for incorporation into a finished dosage form.

A second object of the present invention is the provision of a formulation process which is flexible with respect to the use of different Lenalidomide modifications.

A third object of the present invention is the provision of a pharmaceutical formulation of Lenalidomide that releases Lenalidomide similarly to the branded market product REVLIMID® in all standard media.

It has been found by the inventors of the present application that the abovementioned objectives have been solved by the formulation process and pharmaceutical compositions described hereinafter and the claims.

DETAILED DESCRIPTION OF THE INVENTION

In the present application, several different crystalline modifications of Lenalidomide are investigated:
- Crystalline base form A and form B as examples of Lenalidomide base
- Ammonium chloride cocrystal as an example of a Lenalidomide cocrystal
- Hydrochloric acid salt as an example of a Lenalidomide salt
- DMSO solvate as an example of a Lenalidomide solvate As illustrated in FIGS. 1 to 4, different modifications of Lenalidomide exhibit different types of crystals. Lenalidomide ammonium chloride cocrystal and Lenalidomide hydrochloric acid salt crystallize in a needle-shaped way, whereas Lenalidomide base form A exhibits mainly rod-shaped crystals. Crystals of the Lenalidomide DMSO solvate appear as agglomerates.

As the case for their visual appearance, also the solubility of those different Lenalidomide modifications is quite different. As indicated in table 1, the hydrochloric acid salt is more than 3 times more soluble than the base form B in 0.1M hydrochloric acid at pH1, the solubility of the modifications decreasing in the following order: HCl salt>$NH_4Cl$ cocrystal>DMSO solvate>Base form A>Base form B. On the other hand, the solubilities in acetate buffer and phosphate buffer are much lower, but rather similar.

TABLE 1

| | | Lenalidomide-modification | | | |
|---|---|---|---|---|---|
| Medium | pH-value | Base form B | Base form A | DMSO solvate | $NH_4Cl$ cocrystal | HCl salt |
| 0.1M HCl | 1.0 | 2.74 mg/mL | 4.76 mg/mL | 6.33 mg/ml | 7.76 mg/mL | 9.0 mg/mL |
| Acetate buffer | 4.5 | 0.33 mg/mL | 0.43 mg/mL | 0.38 mg/mL | 0.42 mg/mL | 0.37 mg/mL |
| Phosphate buffer | 6.8 | 0.33 mg/mL | 0.39 mg/mL | 0.35 mg/mL | 0.36 mg/mL | 0.33 mg/mL |

Solubilities are determined by preparing saturated solutions in the three media, followed by HPLC-analysis.

Figure 6:
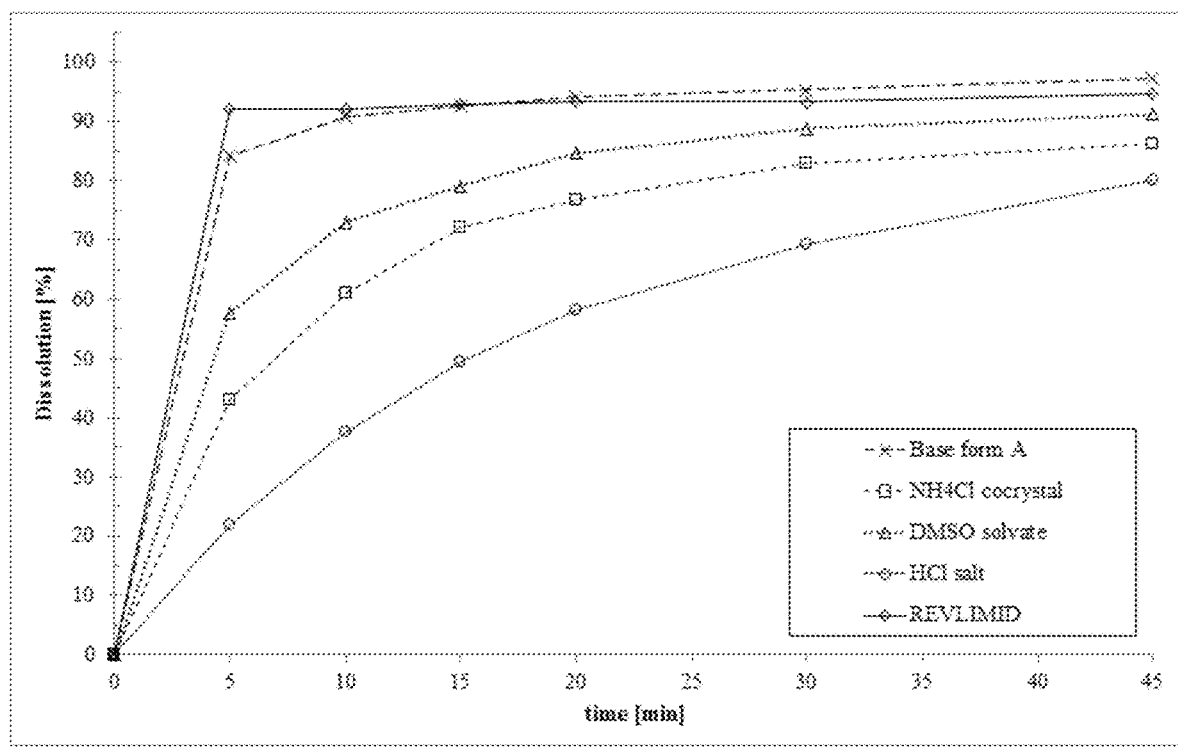
FIG. 6 shows a comparison of the dissolution profiles of capsules manufactured according to reference example 1 with REVLIMID® in 0.1M hydrochloric acid at pH1.

Surprisingly, the dissolution behavior of pharmaceutical compositions comprising different modifications of Lenalidomide appears to be quite unpredictable:

As apparent from FIG. 6, the relative dissolution of the different modifications in 0.1M hydrochloric acid is almost reversed compared to the order of solubility of the polymorphs as indicated in table 1.

Figure 8:
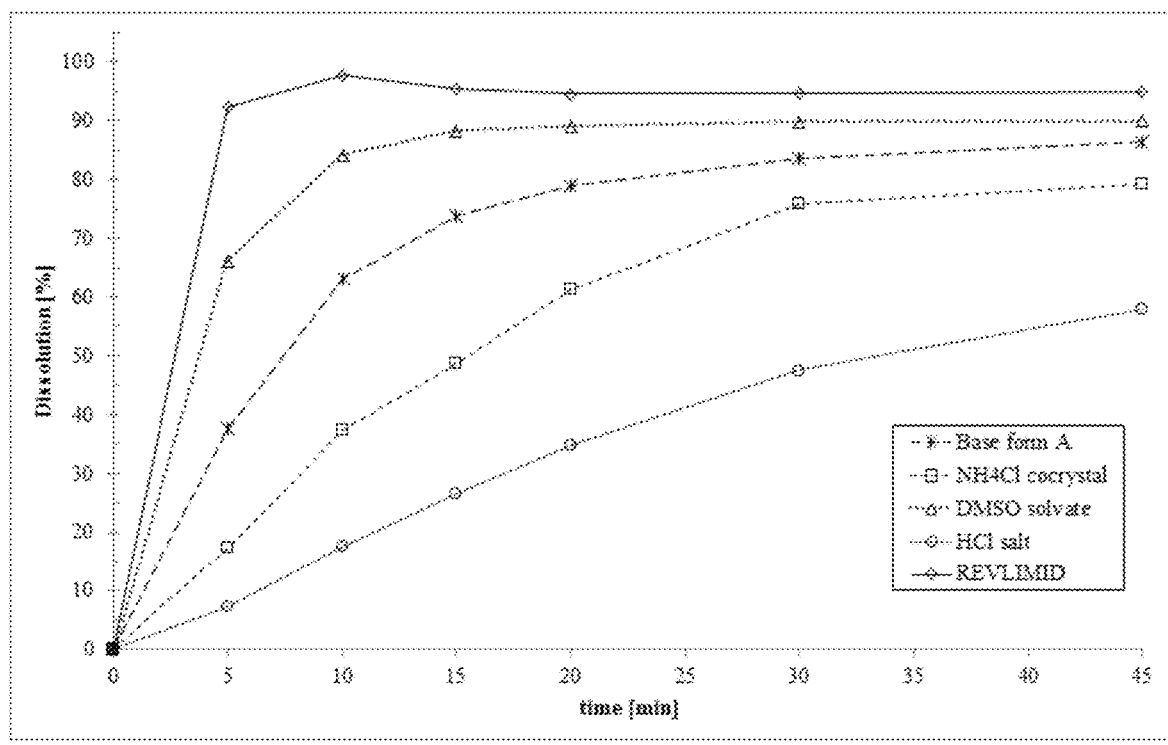
FIG. 8 shows a comparison of the dissolution profiles of capsules manufactured according to reference example 1 with REVLIMID® in acetate buffer solution at pH4.5.
Figure 10:
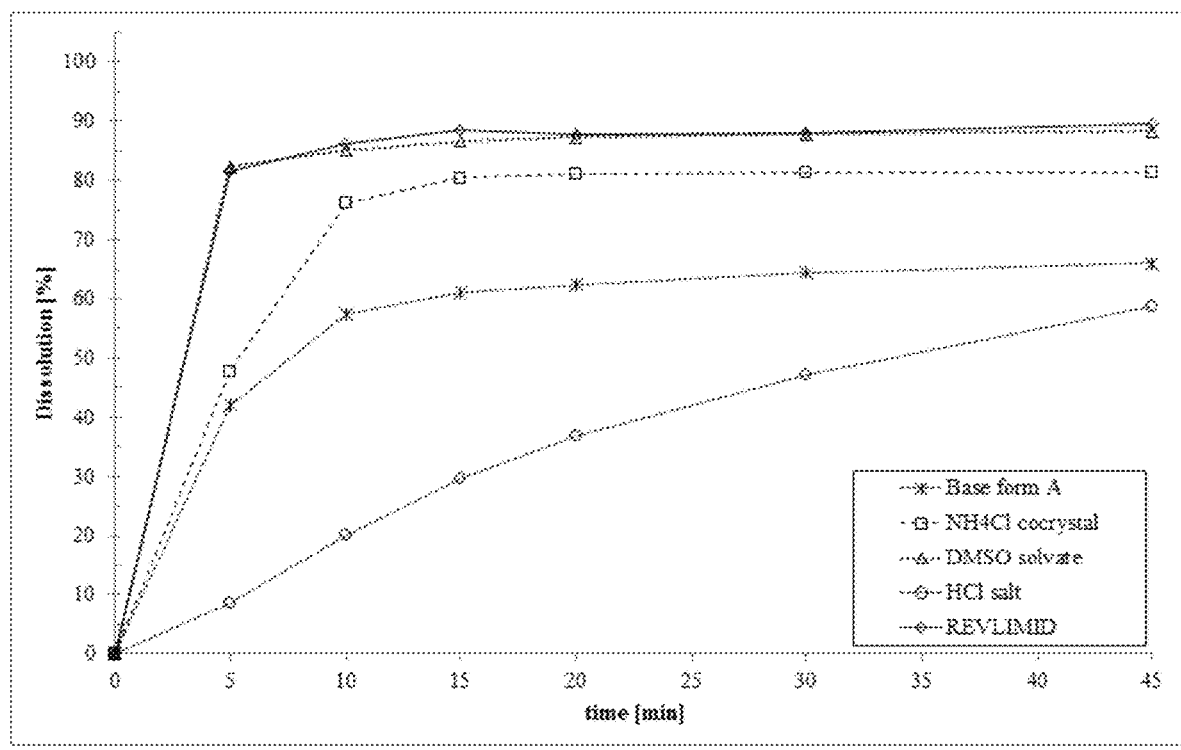
FIG. 10 shows a comparison of the dissolution profiles of capsules manufactured according to reference example 1 with REVLIMID® in phosphate buffer solution at pH6.8.

As apparent from FIGS. 6, 8 and 10, the Lenalidomide hydrochloric acid salt which has the highest solubility exhibits the poorest dissolution rate in all three standard media 0.1M hydrochloric acid at pH1.0, Acetate buffer at pH4.5 and Phosphate buffer at pH6.8.

As further apparent from FIGS. 6, 8 and 10, crystalline Lenalidomide base form A dissolves in 0.1 M hydrochloric acid almost identically compared to the reference product REVLIMID®. Very much unlike REVLIMID®, crystalline Lenalidomide base form A dissolves relatively poor in acetate in phosphate buffer, both media releasing only less than 60% of the active ingredient within 45 min.

The relative dissolution behavior of the different Lenalidomide modifications that were investigated compared to the reference product REVLIMID® in the 3 different standard dissolution media is summarized in table 2.

TABLE 2

| Medium | pH-value | Dissolution rate | | | | | | | |
|---|---|---|---|---|---|---|---|---|---|
| 0.1M HCl | 1.0 | Base form A | > | REVLIMID® | > | DMSO solvate | > | $NH_4Cl$ cocrystal | > HCl salt |
| Acetate buffer | 4.5 | REVLIMID® | > | DMSO solvate | > | Base form A | > | $NH_4Cl$ cocrystal | > HCl salt |
| Phosphate buffer | 6.8 | REVLIMID® | = | DMSO solvate | > | $NH_4Cl$ cocrystal | > | Base form A | > HCl salt |

As can be deducted from table 1 and table 2, the dissolution behavior of the different modifications
- shows no correlation with the corresponding solubilities
- appears to be unpredictably different from each other in different standard media
- appears to be unpredictably different from the reference product REVLIMID®

As a further aspect, the low solubility especially at higher pH-values indicates a low bioavailability which further limits the options for formulation and delivery available for this compound.

Concluding from the facts presented above, it remains a big challenge to develop a formulation which is capable to release Lenalidomide independently from its modification, be it a crystalline form of one of its salts, cocrystals, solvates or base.

In particular, there is a need for pharmaceutical formulations of Lenalidomide that release Lenalidomide similar to the branded market product REVLIMID® in all of the standard media and independently from the choice of the Lenalidomide modification being incorporated.

It has now been found that both requirements are fulfilled by the pharmaceutical compositions according to one of the claims. In accordance, the invention relates to an oral solid pharmaceutical composition comprising
a. from 1.0% to 50.0% by weight, calculated on the basis of Lenalidomide base, of particles of a Lenalidomide modification being selected from a Lenalidomide base, a Lenalidomide salt, a Lenalidomide cocrystal or mixtures thereof;
b. from 50.0% to 99.0% by weight of one or more filler(s); and
c. optionally comprising one or more disintegrant(s), lubricant(s); binder(s), glidant(s) and other pharmaceutically acceptable excipients;

all % by weight—values being calculated relative to the total weight of the composition;

wherein the Lenalidomide particles have a particle size distribution ($d_{90}$) ranging form 20 µm to 100 µm.

Lenalidomide base in the crystalline form A or crystalline form B may be manufactured by known procedures, for example as disclosed in patent application WO 03/097040.

The ammonium chloride ($NH_4Cl$) cocrystal of Lenalidomide may be manufactured according to patent application WO 2013/012485.

Lenalidomide hydrochloride acid (HCl) salt may be manufactured as described in US 2011/0060010 or WO 2011/018101.

The DMSO solvate of Lenalidomide may be manufactured as described in WO 2010/056384.

The amount of Lenalidomide in the pharmaceutical composition according to the present invention is in the range of from 1.0% to 50.0% by weight. In a preferred embodiment, the amount of Lenalidomide is in the range of from 2.0% to 20.0% by weight, more preferably of from 3.0% to 10.0% by weight and most preferred of from 4.0% to 8.0% by weight, calculated on the basis of Lenalidomide base.

In this application, all %-by weight—values are meant to be calculated relative to the total weight of the composition, unless indicated otherwise.

In the present invention, Lenalidomide particles can be particles of Lenalidomide base, a Lenalidomide salt or a Lenalidomide cocrystal.

In the present invention, Lenalidomide particles are characterized by their particle size distribution (PSD), represented by its value.

The $D_{90}$ value is defined such that 90% by volume of the particles have a particle size smaller than the $d_{90}$ value and 10% by volume of the particles have a greater particle size greater than the $d_{90}$ value.

The crystalline Lenalidomide particles in the pharmaceutical compositions exhibit a particle size with a $d_{90}$ of from 1 µm to 1001 µm. In a preferred embodiment, the $d_{90}$-value is between 21 µm and 801 µm, more preferably of from 31 µm to 501 µm and most preferred of from 301 µm to 45 µm.

To obtain the desired particle size, milling of Lenalidomide active pharmaceutical ingredient (API) might be necessary which can be achieved by techniques well known in the art, for example wet milling or dry milling.

In particular, it has been observed that the dissolution rates and, in particular, the overall dissolution of hydrochloric acid salt and $NH_4Cl$-cocrystals may be even more satisfactory if milling by means of a conventional mill is supported by an additional ultrasonification process.

Without wishing to be bound to theory, milling might lead to the formation of secondary agglomerates which are destroyed upon application of the following ultrasonification process developed:
(a) Lenalidomide is dispersed in petrol ether
(b) Ultrasound is applied
(c) Petrol ether is removed by means of filtering the suspension by suction
(d) The solid is dried in air before analysis As apparent from FIGS. 9 and 11, the application of this milling technique leads to a further approximation to the dissolution profile of REVLIMID® for $NH_4Cl$ cocrystal and Lenalidomide HCl salt.

The pharmaceutical compositions according to the present invention further comprise pharmaceutical suitable excipients like one or more filler(s), one or more binder(s) and one or more disintegrant(s) and optionally one or more lubricant(s), one or more glidant(s) and other pharmaceutically acceptable excipient(s). The terms filler(s), binder(s), disintegrant(s), lubricant(s), glidant(s), excipient(s) etc. shall be understood as including a single compound but also mixtures of compounds.

Pharmaceutically acceptable filler(s) include, but are not limited to microcrystalline cellulose (MCC), silicified microcrystalline cellulose (SMCC), lactose, mannitol, sucrose, di calcium phosphate, calcium carbonate, magnesium carbonate, pregelatinized starch, low substituted hydroxypropyl cellulose (L-HPC), powder cellulose, calcium silicate, calcium phosphate, sorbitol, mannitol, dextrines, kaolin, magnesium oxide, calcium sulfate, xylitol, isomalt, glucose, fructose, maltose, acids like citric acid, tartaric acid, fumaric acid and co-polymers from vinyl pyrrolidone and vinyl acetate or co-polymers of polyethylene glycol. The preferred filler(s) are microcrystalline cellulose (MCC) and lactose anhydrous.

The amount of filler(s) is in the range between 40.0% to 95.0% by weight. In a preferred embodiment, the amount of filler(s) is in the range between 85.0% to 90.0% by weight.

Pharmaceutically acceptable disintegrant(s) include, but are not limited to croscarmellose, calcium carboxymethylcellulose, sodium starch glycolate, maize starch, pregelatinized starch, potato starch, alginic acid, polyvinylpyrrolidone (crospovidone) and low substituted hydroxypropyl cellulose (L-HPC). Preferred disintegrant is sodium croscarmellose.

Pharmaceutically acceptable lubricant(s) include, but are not limited to, magnesium stearate, calcium stearate, sodium stearate, stearic acid, sodium glyceryl behenate, hexanedioic acid, hygrogenated vegetable oil, sodium stearyl fumarate and glycerine fumarate. Preferred lubricant is magnesium stearate.

Pharmaceutically acceptable binder(s) include, but are not limited to, hydroxypropyl methylcellulose (HPMC), dihydroxy propyl cellulose, methyl cellulose, hydroxyethyl cellulose, ethyl cellulose, sodium carboxyl methylcellulose, polyethylene glycol, maltodextrin, pregelatinized starch, starch, polymethacrylates, sodium alginate, polyvinylpyrrolidone (povidone) and vinylpyrrolidone/vinylacetate copolymer (copovidone).

Pharmaceutically acceptable glidant(s) include, but are not limited to colloidal silicone dioxide, talc and magnesium carbonate.

The preferred pharmaceutical composition is a capsule.

The manufacturing process of the capsules according to the present invention comprises the following steps:
(a) Lenalidomide is blended with one or more filler(s) to obtain blend 1;
(b) blend 1 is blended with one or more filler(s) to obtain blend 2;
(c) blend 2 is blended with one or more disintegrant(s) and one or more lubricant(s) to obtain blend 3;
(d) blend 3 is sifted
(e) blend 2 and blend 3 are blended;
(f) the final blend is filled into the appropriate capsule.

Figure 1:
FIG. 1 shows a photograph of Lenalidomide hydrochloric acid salt crystals manufactured according to reference example 1.
Figure 2:
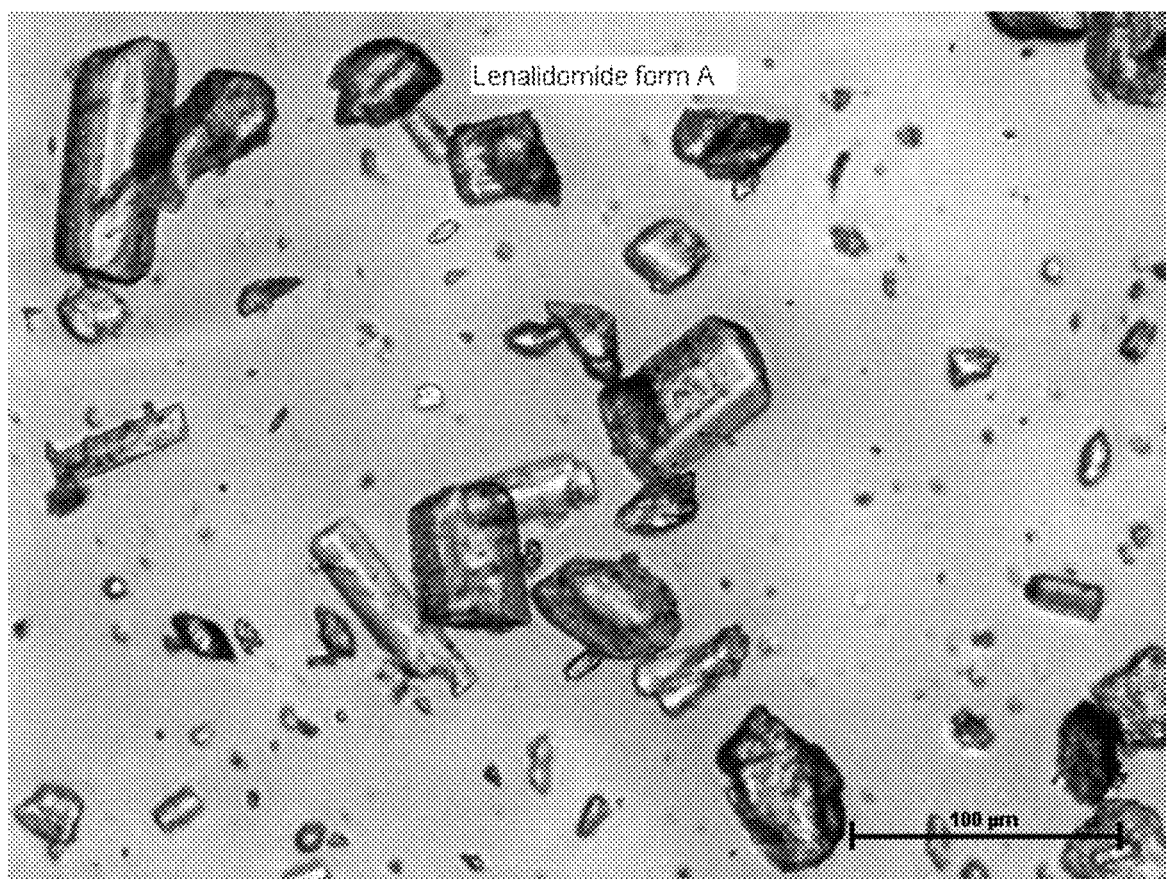
FIG. 2 shows a photograph of Lenalidomide base form A crystals manufactured according to reference example 1.
Figure 3:
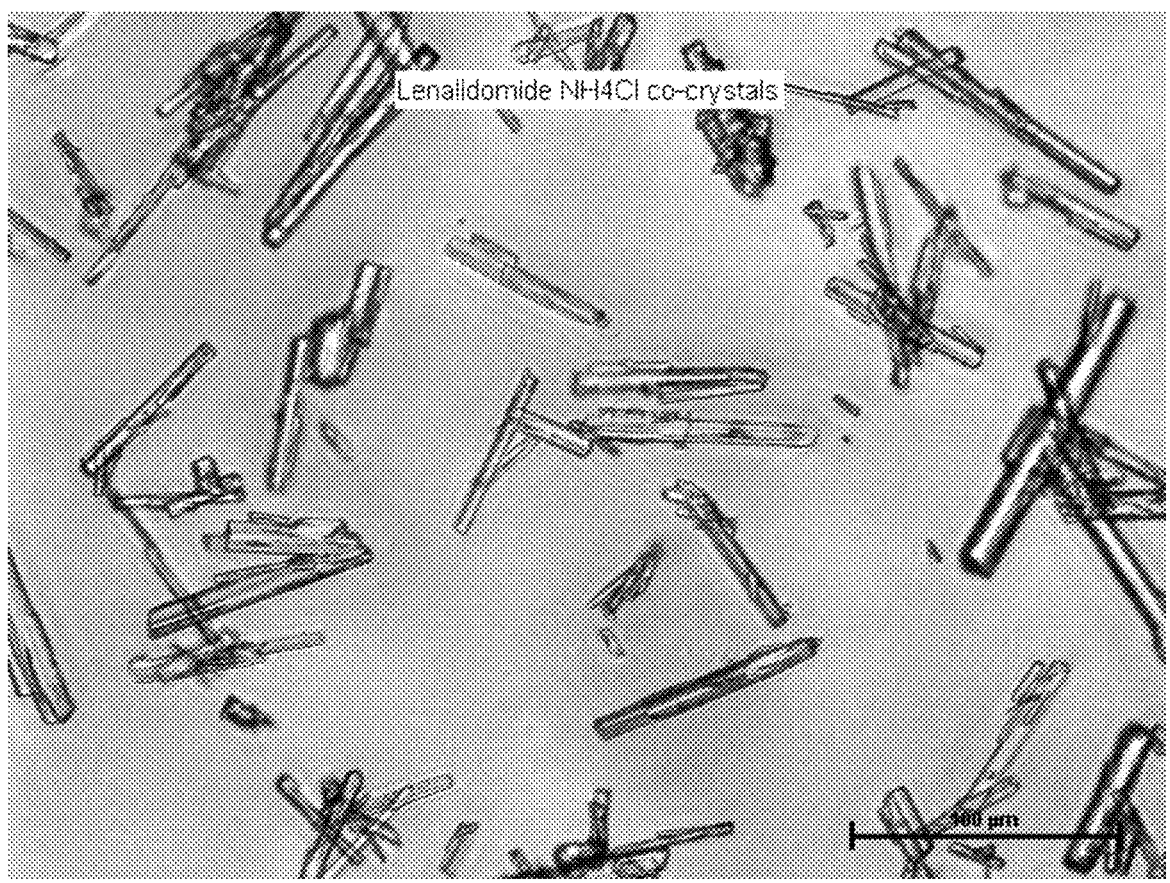
FIG. 3 shows a photograph of Lenalidomide ammonium chloride cocrystals manufactured according to reference example 1.
Figure 4:
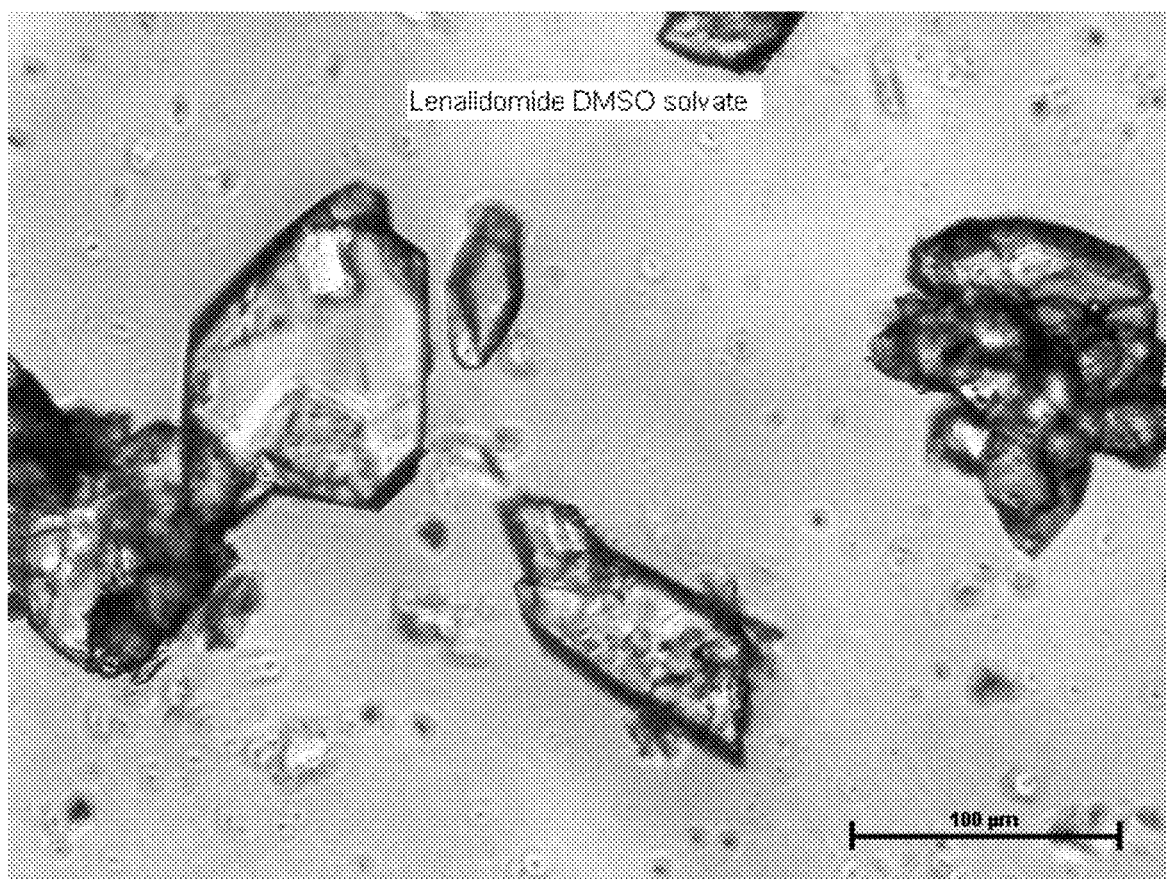
FIG. 4 shows a photograph of Lenalidomide DMSO-solvate crystals manufactured according to reference example 1.
Figure 5:
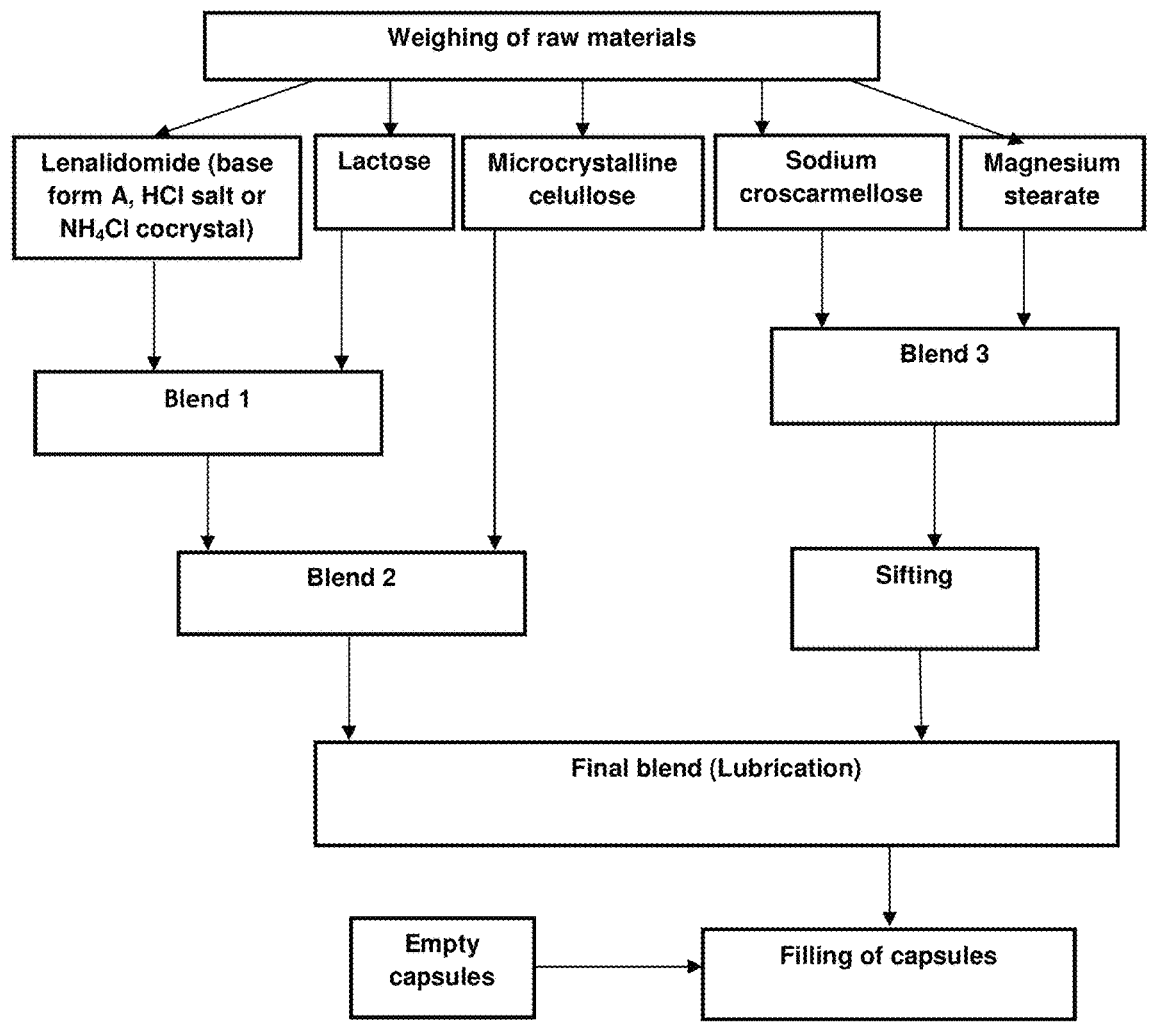
FIG. 5 shows a detailed flow chart of the manufacturing process of Lenalidomide capsules according to inventive example 2.

A detailed flow chart of the manufacturing process is displayed in FIG. 5.

Surprisingly and advantageously, this simple dry-powder-blending process is suitable for the incorporation of any of Lenalidomide base form A, Lenalidomide hydrochloride salt and Lenalidomide ammonium chloride cocrystal without the need to adjust any process parameter.

In contrast to other manufacturing techniques such as wet granulation that might lead to the formation of higher aggregated API-particles, a further advantage of the dry-powder-blending process according to the present invention is that the size of the Lenalidomide particles does not change during the formulation process, but remains the same from the API stage through the readily filled capsule.

A preferred embodiment of the present invention is an oral solid pharmaceutical composition comprising
a. from 2.0% to 20.0% by weight of a Lenalidomide in the modification base form A
b. from 60.0% to 98.0% by weight of one or more filler(s);
c. from 1.0% to 10.0% by weight of one or more disintegrant(s); and
d. from 0.5% to 2.0% by weight of one or more lubricant(s)

all % by weight—values being relative to the total weight of the composition calculated on the basis of Lenalidomide base; wherein the Lenalidomide particles have a particle size distribution ($d_{90}$) of between 1 μm and 100 μm.

EXAMPLES

Particle Size Studies
 i. Experimental Setup

| System | Malvern "Mastersizer 2000" |
|---|---|
| Dispersion Unit | Hydro 2000 |
| Sample dispersion way | Wet way |
| liquid medium | Cyclohexane |

Parameters for the Analysis

TABLE 5

| Measurement time | 6 s |
|---|---|
| Laser concentration | 5-10% |
| Pump speed | 2 200 rpm |
| Optical model | Fraunhofer | ii. Preparation of Solutions
Sample solution. Place 50 mg of well mixed sample to a 100 mL beaker. Add 25 mL of cyclohexane. Using Pasteur pipette transfer small aliquots of sample slurry to the measuring cuvette until the concentration reading is good. The beaker is swirled efficiently before each pipetting.
 iii. Analytical Procedure
Measurement according to the operating instructions. Perform three successive determinations, from which calculate the mean value.

Dissolution Testing Method
The in-vitro dissolution according to examples 2 to 5 were analyzed according to Ph. Eur. 2.9.3/USP <711>—Method 2 (Paddle Apparatus) with the settings as displayed in table 7.

TABLE 7

| Apparatus | "paddle" |
|---|---|
| Media: | |
| pH 1.0 | 0.1M Hydrochloric acid |
| pH 4.5 | Acetate buffer |
| pH 6.8 | Phosphate buffer |
| Volume: | 900 ml |
| Temperature: | 37.0° C. ± 0.5° C. |
| Method | UV-247 nm |
| Rotation speed: | 50 rpm |
| Filter | Glass microfiber filter GF/D |

HPLC Conditions:

TABLE 8

| Column: | GL Science Inc. Inertsil ODS-3V 4.6 × 150 mm, 5.0 μm or equivalent |
|---|---|

TABLE 8-continued

| Column temperature | 25° C. |
|---|---|
| Sample temperature | 25° C. |
| Mobile phase | mixture of buffer solution pH3.5, acetonitrile and methanol in volume ratios 70:12:18 |
| Sample diluent | dissolution medium |
| Flow rate | 1.0 mL/min |
| Injection volume | 20 μL |
| Run time | 6 min |
| Injector wash solvent | 10 per cent methanol |
| Detection | UV at 210 nm |

Preparation of the Solutions:
Buffer solution pH3.5. Dissolve 1.36 g of potassium dihydrogen phosphate in 900 mL of water for chromatography. Adjust pH of prepared solution to 3.5 with phosphoric acid (10 percent) and dilute to 1000 mL with water for chromatography, mix. Filter through membrane filter with pore size not more than 0.45 μm.

Standard solution. Accurately weigh approximately 35 mg of Lenalidomide in-house reference substance, transfer in to 25 mL volumetric flask, dissolve in 10 mL of methanol, sonicate for 5 minutes and make to the volume with the dissolution medium, mix. Dilute 1.0 mL of this solution to 50 ml with dissolution medium. Prepare 2 standard solutions. System suitability. Use the chromatograms obtained with the standard solution.

Symmetry factor of principal peak should be in range between 0.8 and 1.5. Theoretical plate number of principal peak should be not less than 2000. Relative standard deviation between three injections should be not more than 2.0 percent.

Analytical Procedure and Calculations
Equilibrate chromatographic system at a flow rate 1.0 mL/min not less than 30 min. Inject into the column solutions in the following order:
 sample diluent (dissolution medium);
 standard solution—three times each;
 test solution—one time each.

Record the chromatograms and measure the peak areas.
The content of lenalidomide (X), percent of declared, calculate by formula:

$$X = \frac{S_{an} \times m_{st} \times V_{an} \times C_{st}}{S_{st} \times V_{st} \times n_{st} \times a},$$

$S_{an}$—principal peak area in the test solution chromatogram;
$S_{st}$—principal peak area in the standard solution chromatogram;
$m_{st}$—weight of lenalidomide In-house reference substance, mg;
$V_{st}$—volume of the standard solution, mL (25);
$n_{st}$—dilution of the standard solution, times (50);
$C_{st}$—assay of lenalidomide In-house reference substance, percent;
a—declared content of lenalidomide per capsule, 25 mg;
$V_{an}$—volume of the dissolution medium for test solution, mL (900).

Assay of lenalidomide is calculated by first standard, if standards verification is between 98.0 percent to 102.0 percent.

Standard verification, percent, calculate by formula:

$$X = \frac{S_{st.2} \times m_{st.1}}{S_{st.1} \times m_{st.2}} \times 100 \text{ per cent,}$$

$S_{st.1}$—principal peak area in the standard solution No. 1 chromatogram;
$m_{st.1}$—weight of lenalidomide In-house reference substance No. 1, mg;
$S_{st.2}$—principal peak area in the standard solution No. 2 chromatogram;
$m_{st.2}$—weight of lenalidomide In-house reference substance No. 2, mg;
100—recalculation coefficient from part mass to percent.

Example 1 (Reference)

Lenalidomide base in the crystalline form A was prepared as described in patent application WO 03/097040.

Ammonium chloride ($NH_4Cl$) cocrystal of Lenalidomide was prepared as described in patent application WO 2013/012485.

Lenalidomide hydrochloride acid (HCl) salt was prepared as described in patent application US 2011/0060010.

Lenalidomide DMSO solvate was prepared as described in patent application WO 2010/056384.

The resulting particle sizes are displayed in table 3.

TABLE 3

| Lenalidomide modification | PSD, $d_{90}$ |
|---|---|
| Base form A | 219 µm |
| HCl salt | 434 µm |
| $NH_4Cl$ cocrystal | 383 µm |

The pharmaceutical compositions were prepared according to the process displayed in FIG. 5 with the amounts of excipients according to table 4.

TABLE 4

| Strength | 2.5 mg | 5 mg | 10 mg | 15 mg | 25 mg | percent w/w* |
|---|---|---|---|---|---|---|
| Lenalidomide active substance** | 2.5 mg | 5.0 mg | 10.0 mg | 15.0 mg | 25.0 mg | 5.0% |
| Excipients: | | | | | | |
| Lactose anhydrous | 28 mg | 56 mg | 132 mg | 168 mg | 280 mg | 56.0% |
| Microcrystalline cellulose | 17.5 mg | 35 mg | 70 mg | 105 mg | 175 mg | 35.0% |
| Sodium croscarmellose | 1.5 mg | 3 mg | 6 mg | 9 mg | 15 mg | 3.0% |
| Magnesium stearate | 0.5 mg | 1 mg | 2 mg | 3 mg | 5 mg | 1.0% |
| Total weight of capsule content | 50 mg | 100 mg | 200 mg | 300 mg | 500 mg | 100.0% |

*Relative amount, based on the weight of the total composition
**Calculated on the basis of Lenalidomide base The dissolution profiles of pharmaceutical compositions according to reference example 1 in 0.1M hydrochloric acid at pH1.0, Acetate buffer at pH4.5 and phosphate buffer at pH6.8 are displayed in FIGS. 6, 8 and 10, respectively.

Example 2—Pharmaceutical Compositions According to the Invention

Lenalidomide base in the crystalline form A, Lenalidomide ammonium chloride ($NH_4Cl$) cocrystal and Lenalidomide hydrochloride acid (HCl) salt were prepared as described in reference example 1, followed by a milling step (15 min at 20 Hz, Retsch MM301 Mixer Mill with 35 mL stainless steel grinding jar with 20 mm diameter stainless steel balls).

The resulting particle sizes are displayed in table 6.

TABLE 6

| Lenalidomide API form | PSD, $d_{90}$ |
|---|---|
| Hydrochloride salt | 43 µm |
| Ammonium chloride cocrystal | 31 µm |
| Base form A | 35 µm |

The pharmaceutical compositions were prepared according to the process displayed in FIG. 5 with the amounts of excipients as displayed in table 4.

Figure 7:
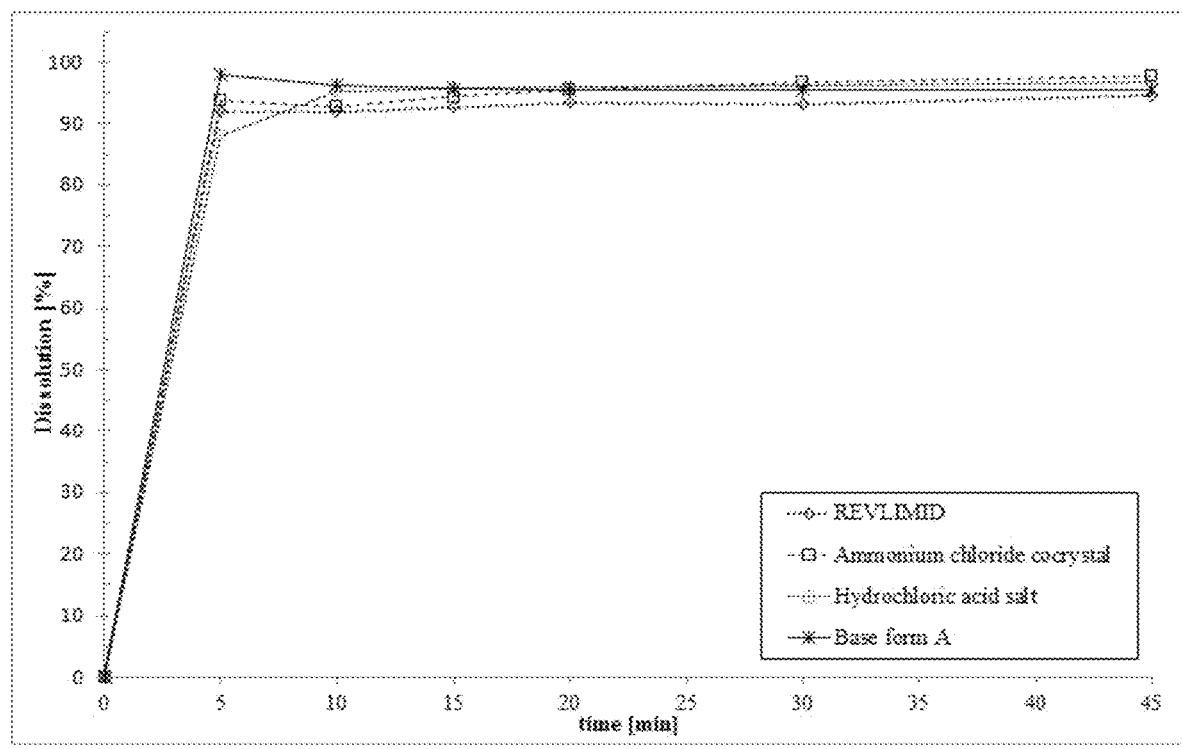
FIG. 7 shows a comparison of the dissolution profiles of capsules manufactured according to inventive example 2 with REVLIMID® in 0.1M hydrochloric acid at pH1.
Figure 9:
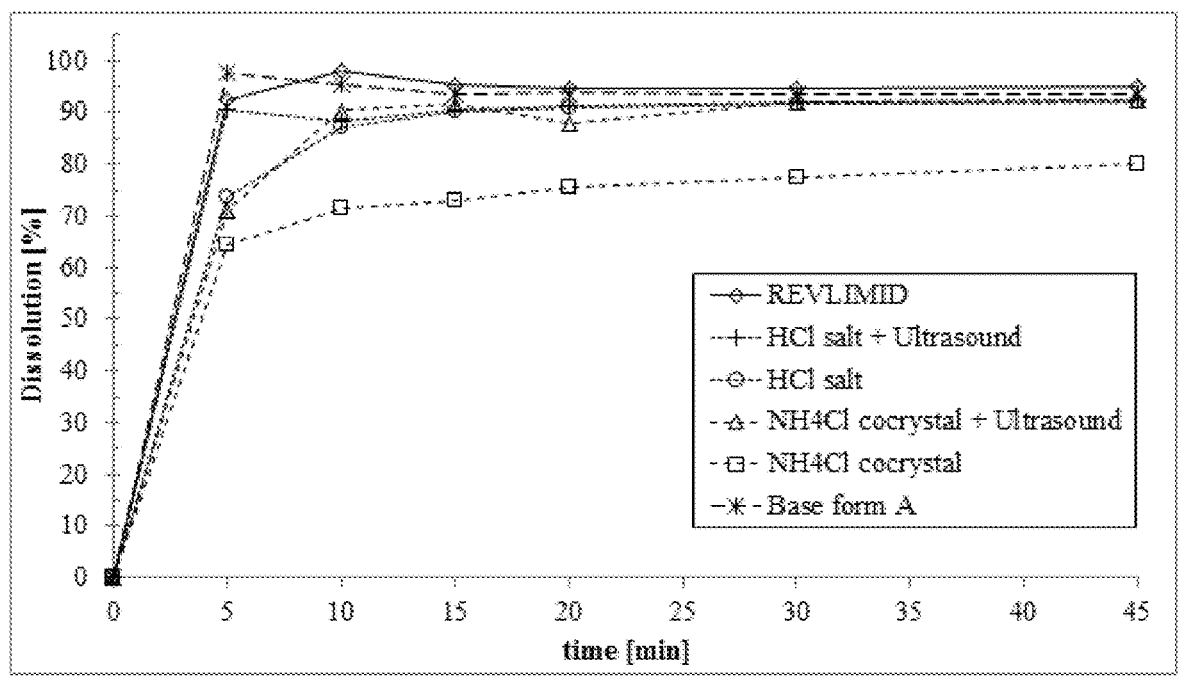
FIG. 9 shows a comparison of the dissolution profiles of capsules manufactured according to inventive example 2 with REVLIMID® in acetate buffer solution at pH4.5.
Figure 11:
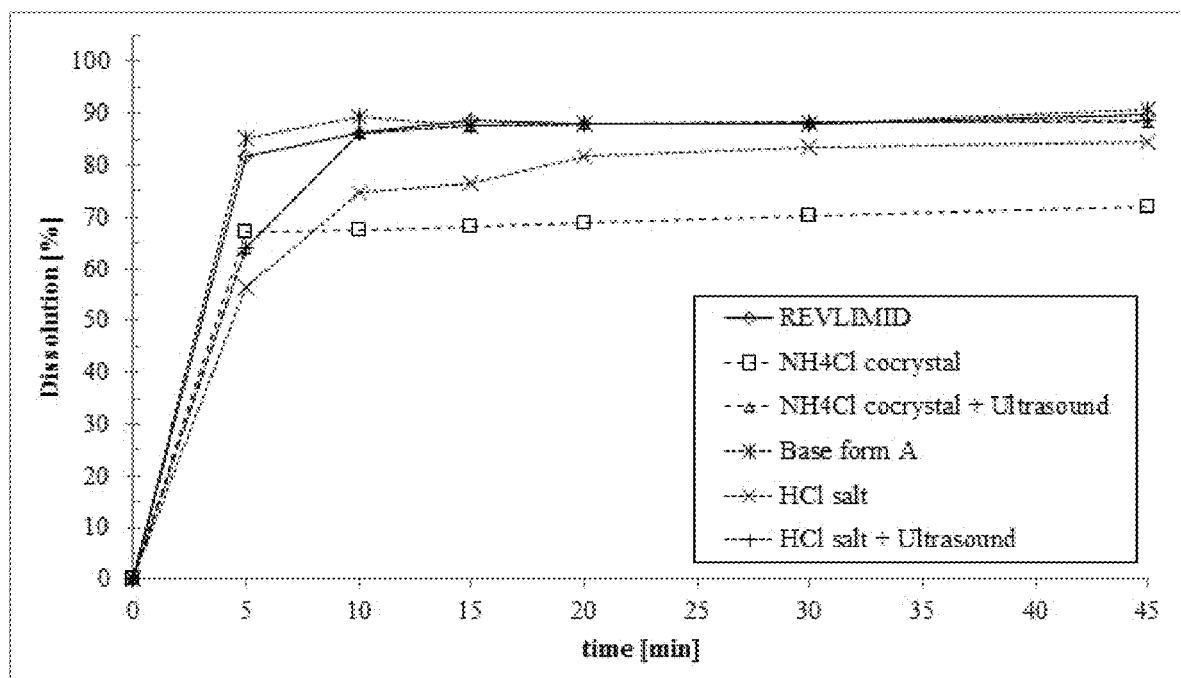
FIG. 11 shows a comparison of the dissolution profiles of capsules being manufactured according to inventive example 2 with REVLIMID® in phosphate buffer solution at pH6.8.

The dissolution profiles of pharmaceutical compositions according to reference example 1 in 0.1M hydrochloric acid at pH1.0, acetate buffer at pH4.5 and phosphate buffer at pH6.8 are displayed in FIGS. 7, 9 and 11, respectively.

Results:

As can be deducted from a comparison of FIGS. 6, 8 and 10 with FIGS. 7, 9 and 11, pharmaceutical compositions being manufactured according to inventive example 2 exhibit an almost identical dissolution profile in all standard media (0.1M hydrochloric acid at pH1.0, acetate buffer at pH4.5 or phosphate buffer at pH6.8) independent from the modification of Lenalidomide being incorporated in the capsule, be it Lenalidomide base form A, Lenalidomide hydrochloride salt or Lenalidomide ammonium chloride cocrystal.

In other words, the dissolution profiles of the pharmaceutical compositions according to the present invention are indifferent as regards the modification of Lenalidomide incorporated in the pharmaceutical composition. This is quite surprising since
- the intrinsic solubilities of the different modifications are quite different, as apparent from table 1
- the dissolution behavior of formulations according to reference example 1 shows no correlation with the corresponding intrinsic solubilities
- the dissolution behavior of formulations according to reference example 1 appears to be unpredictably different from each other in different standard media, depending on the modification of Lenalidomide.

In addition to the observation above and as further apparent from a comparison of the experimental results, the dissolution profiles of the pharmaceutical compositions according to example 2 of the present invention do not exhibit a significant difference compared to the reference product REVLIMID®. This is even more surprising since,
- the dissolution behavior of formulations according to reference example 1 appears to be unpredictably different from the reference product REVLIMID® in each standard medium
- to the best of the knowledge of the inventors of the present application, none of the modifications investigated by the inventors of the present application is used in REVLIMID®.

Example 3—Pharmaceutical Compositions According to the Invention

The pharmaceutical compositions were prepared as described in example 2, with the difference that the pharmaceutical compositions were prepared with the amounts of excipients according to table 9.

TABLE 9

| Strength | 25 mg | percent w/w* |
|---|---|---|
| Lenalidomide active substance** | 25.0 mg | 6.25% |
| Lactose anhydrous | 200.0 mg | 50.0% |
| Microcrystalline cellulose | 159.0 mg | 39.75% |
| Sodium croscarmellose | 12.0 mg | 3.0% |
| Magnesium stearate | 4.0 mg | 1.0% |
| Total weight of capsule content | 400.0 mg | 100.0% |

*Relative amount, based on the weight of the total composition
**Calculated on the basis of Lenalidomide base Example 4—Pharmaceutical Compositions According to the Invention Stability data obtained for pharmaceutical compositions according to example 3 are as displayed in table 10 and table 11 below:
a) Lenalidomide $NH_4Cl$ cocrystal, storage conditions 25° C., 60% RM, strength=25 mg

TABLE 10

| Time [month] | Water content [%], n = 3 | Assay [%], n = 10 |
|---|---|---|
| 0 | 1.83 | 99.9 |
| 3 | 1.9 | 98.3 |
| 6 | 1.9 | 100.2 | b) Lenalidomide base form A, storage conditions 25° C., 60% RM, strength=25 mg

TABLE 11

| Time [month] | Water content [%] | Assay [%] |
|---|---|---|
| 0 | 2.44 | 97.5 |
| 3 | 2.1 | 99.5 |
| 6 | 2.2 | 98.1 |

As can be deducted from tables 10 and 11, the pharmaceutical compositions according to the present invention show sufficient

The invention claimed is:

1. An oral solid pharmaceutical composition comprising
   a. from 1.0% to 50.0% by weight, calculated on the basis of Lenalidomide base, of particles of a Lenalidomide modification, wherein the Lenalidomide modification is Lenalidomide base form A;
   b. from 50.0% to 99.0% by weight of one or more filler(s); and
   c. optionally comprising one or more disintegrant(s), lubricant(s); binder(s), glidant(s) and other pharmaceutically acceptable excipients;
all % by weight-values being calculated relative to the total weight of the composition;
wherein the particle size distribution ($d_{90}$) of the Lenalidomide particles is in the range of from 3 μm to 50 μm.

2. The oral solid pharmaceutical composition according to claim 1, wherein the amount of particles of a Lenalidomide modification is in the range of from 2.0% to 20.0% by weight.

3. The oral solid pharmaceutical composition according to claim 2, wherein the amount of particles of a Lenalidomide modification is in the range of from 3.0% to 10.0% by weight.

4. The oral solid pharmaceutical composition according to claim 2, wherein the amount of particles of a Lenalidomide modification is in the range of from 4.0% to 8.0% by weight.

5. The oral solid pharmaceutical composition according to claim 1, wherein the particle size distribution ($d_{90}$) of the Lenalidomide particles is in the range of from 30 μm to 45 μm.

6. The oral solid pharmaceutical composition according to claim 1, wherein the one or more filler(s) are selected from microcrystalline cellulose (MCC), silicified microcrystalline cellulose (SMCC), lactose monohydrate, lactose anhydrous, mannitol, sucrose, di calcium phosphate, calcium carbonate, magnesium carbonate, pregelatinized starch, low substituted hydroxypropyl cellulose (L-HPC), powder cellulose, calcium silicate, calcium phosphate, sorbitol, mannitol, dextrines, kaolin, magnesium oxide, calcium sulfate, xylitol, isomalt, glucose, fructose, maltose, acids and co-polymers selected from the group consisting of vinyl pyrrolidone and vinyl acetate or co-polymers of polyethylene glycol.

7. The oral solid pharmaceutical composition according to claim 6, wherein the one or more filler(s) are selected from MCC and lactose anhydrous.

8. The oral solid pharmaceutical composition according to claim 1, wherein the one or more disintegrant(s) are selected from croscarmellose, calcium carboxymethylcellulose, sodium starch glycolate, maize starch, pregelatinized starch, potato starch, alginic acid, polyvinylpyrrolidone (crospovidone) and low substituted hydroxypropyl cellulose (L-HPC).

9. The oral solid pharmaceutical composition according to claim 8, wherein the one or more disintegrant(s) is croscarmellose sodium.

10. The oral solid pharmaceutical composition according to claim 1, wherein the one or more lubricant(s) are selected from magnesium stearate, calcium stearate, sodium stearate, stearic acid, sodium glyceryl behenate, hexanedioic acid, hygrogenated vegetable oil sodium, stearyl fumarate and glycerine fumarate.

11. The oral solid pharmaceutical composition according to claim 10, wherein the one or more lubricant(s) is magnesium stearate.

12. The oral solid pharmaceutical composition according to claim 1, wherein the one or more binder(s) are selected from the group consisting of hydroxypropyl methylcellulose (HPMC), dihydroxy propyl cellulose, methyl cellulose, hydroxyethyl cellulose, ethyl cellulose, sodium carboxyl methylcellulose, polyethylene glycol, maltodextrin, pregelatinized starch, starch, polymethacrylates, sodium alginate, polyvinylpyrrolidone (povidone) and vinylpyrrolidone/vinylacetate copolymer (copovidone).

13. The oral solid pharmaceutical composition according to claim 1, wherein the one or more glidant(s) are selected from colloidal silicone dioxide, talc and magnesium carbonate.

14. The oral solid pharmaceutical composition according to claim 1 in form of a capsule, wherein
   i. the amount of filler(s) is in the range of from 60.0% to 98.0% by weight;
   ii. the amount of one or more disintegrant(s) is in the range of from 1.0% to 10.0% by weight
   iii. the amount of one or more lubricant(s) is in the range of from 0.5% to 2.0% by weight.

15. The capsule according to claim 14, wherein the amount of filler(s) is in the range of from 80.0% to 95.0% by weight.

16. A dry powder blending process for the manufacture of oral solid pharmaceutical compositions in form of a capsule according to claim 14, comprising the steps of:
   a. Milling a crystalline Lenalidomide base form A;
   b. Blending the milled Lenalidomide and first part of the filler(s) to obtain blend 1;
   c. Blending of blend 1 and second part of the filler(s) to obtain blend 2;
   d. Blending of disintegrant(s) and lubricant(s) to obtain blend 3;
   e. Sifting of blend 3;
   f. Blending of blend 2 and blend 3 (Lubrication) to obtain the final blend;
   g. Filling of capsules with the final blend.

17. The process for the manufacture of a capsule according to claim 16, comprising the steps of:
   a. Milling a crystalline Lenalidomide base form A;
   b. Blending the milled Lenalidomide and lactose to obtain blend 1;
   c. Blending of blend 1 and Microcrystalline cellulose to obtain blend 2;
   d. Blending of sodium croscarmellose and magnesium stearate to obtain blend 3;
   e. Sifting of blend 3;
   f. Blending of blend 2 and blend 3 to obtain the final blend; and
   g. Filling of capsules with the final blend.

18. The oral solid pharmaceutical composition according to claim 6, wherein the one or more fillers are selected from the group consisting of citric acid, tartaric acid, and fumaric acid.

* * * * *